(12) United States Patent
Woloszynek (10) Patent No.: US 7,745,523 B1
(45) Date of Patent: Jun. 29, 2010

(54) COUPLING COMPOUNDS AND THEIR USES IN RUBBER COMPOSITIONS AND TIRES

(75) Inventor: Robert Alan Woloszynek, Brunswick, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 12/329,885

(22) Filed: Dec. 8, 2008

(51) Int. Cl.
*B60C 1/00* (2006.01)
*C08K 5/55* (2006.01)

(52) U.S. Cl. ........................ 524/262; 524/183

(58) Field of Classification Search ............ 524/262
See application file for complete search history.

(56) References Cited

U.S. PATENT DOCUMENTS

| | | | |
|---|---|---|---|
| 6,111,000 A * | 8/2000 | Materne et al. | 524/183 |
| 6,214,911 B1 | 4/2001 | Materne et al. | |
| 6,229,039 B1 | 5/2001 | Materne et al. | |
| 6,353,072 B1 | 3/2002 | Towns et al. | |
| 7,279,531 B1 | 10/2007 | Halasa et al. | |
| 2001/0036994 A1 | 11/2001 | Bergemann et al. | |
| 2007/0237840 A1 | 10/2007 | Chern et al. | |

FOREIGN PATENT DOCUMENTS

| | | |
|---|---|---|
| EP | 0 941 995 A2 | 9/1999 |
| EP | 1 136526 A1 | 9/2001 |
| WO | 2007015536 A1 | 2/2007 |

OTHER PUBLICATIONS

STIC search results, Jul. 2, 2009.*
STIC search results, Jul. 30, 2009.*
Ferguson et al. Journal of Organometallic Chemistry, 526, 195-198, 1996.
Grant et al. J. Am. Chem. Soc., 86, 3012-3017, 1964.
Kim et al. Geochimica et. Cosmochimica Acta, 70, 3231-3238, 2006.
Leino et al., Tetrahedron Letters, 45, 8489-8491, 2004.

* cited by examiner

*Primary Examiner*—Ling-Siu Choi
*Assistant Examiner*—Hui Chin
(74) *Attorney, Agent, or Firm*—Wood, Herron & Evans, L.L.P.

(57) ABSTRACT

The invention includes coupling compounds, rubber compositions, and tires. The coupling compounds can, for example, be used to couple to silica filler. Rubber compositions can comprise the coupling compound and polymers. Polymers can be homopolymers, copolymers and terpolymers, and can include repeat units provided from conjugated diene monomers. Tires and various parts of tires can be made from those rubber compositions.

20 Claims, 5 Drawing Sheets

COUPLING COMPOUNDS AND THEIR USES IN RUBBER COMPOSITIONS AND TIRES

BACKGROUND

It is sometimes desirable for tires to have a combination of good wet skid resistance, low rolling resistance, tear strength, and good wear characteristics. Wear characteristics of a tire tread can be difficult to improve without sacrificing traction and/or rolling resistance. Sometimes, such properties depend upon dynamic viscoelastic properties of the tire tread rubber composition and the components utilized in the rubber composition.

In order to reduce the rolling resistance and to improve the tread wear characteristics of tires, rubbers or polymers having a high rebound physical property (low hysteresis) have been used for the tire tread rubber compositions. However, in order to increase the wet skid resistance of a tire tread, elastomers that have a relatively lower rebound physical property (higher hysteresis) which thereby undergo a greater energy loss, have sometimes been used for such tread rubber compositions. To achieve such relatively inconsistent viscoelastic properties for the tire tread rubber compositions, blends of various types of synthetic and natural rubber can be utilized in tire treads.

It can be desirable for synthetic rubbery polymers to exhibit relatively low levels of hysteresis (indicated by relatively higher rebound values). This can be important when elastomers are used in tire tread rubber compositions. In practice, the elastomers can be conventionally blended with sulfur curative, rubber reinforcing fillers such as, for example precipitated silica and rubber reinforcing carbon black, sulfur vulcanization accelerators, rubber antidegradants and other desired rubber chemicals and are then subsequently vulcanized, or cured, under pressure at an elevated temperature in a suitable mold. The physical properties of such cured rubber compositions can depend upon the degree to which the rubber reinforcing fillers, such as carbon black or silica, are homogeneously dispersed throughout the elastomer. In some instances, the degree of homogeneity of the dispersement of the reinforcing filler relates, at least in part, to the degree of affinity that carbon black or silica have for the rubbery polymer.

Amorphous silica reinforcement has sometimes been used in combination with rubber reinforcing carbon black to promote lower rolling resistance (e.g. better vehicular fuel economy) and to promote better traction (e.g. skid and braking resistance) for a tire tread rubber composition. However, use of such silica reinforcement filler, as compared to rubber reinforcing carbon black, can result in a decrease in wear resistance (e.g. increase in tread wear) of a tire tread rubber composition.

Thus, it can be desirable to provide coupling compounds, rubber compositions, and tires made therefrom to overcome the above-described issues as well as others.

SUMMARY

The invention includes coupling compounds, as well as rubber compositions and tires incorporating the coupling compounds. The coupling compounds include and In these coupling compounds, n can be the same or different and can be 2, 3, or about 4; R can be the same or different and can be alkylene or arylene with from about 1 to about 18 carbons; $R^1$ can be —OH or —OCH$_2$CH$_2$OCH$_2$CH$_2$OCH$_3$; $R^2$ can be the same or different and is bivalent alkylene or arylene with about 1 to about 18 carbons.

The coupling compounds can be formed, for example, by reacting thiols with SO$_2$Cl$_2$.

In still other embodiments, rubber compositions comprising the coupling compound, polymer and filler are provided. Tires can be made from these rubber compositions.

BRIEF DESCRIPTION OF THE DRAWINGS

The following detailed description of specific embodiments of the present invention can be better understood when read in conjunction with the following drawings.

DETAILED DESCRIPTION

The present invention relates to coupling compounds, rubber compositions, and tires made therefrom. In some embodiments, the present invention relates to a rubber composition that comprises at least one coupling compound.

The coupling compound can be selected from:

n can be the same or different and can be 2, 3, or about 4. R can be the same or different and can be alkylene or arylene having from about 1 to about 18 carbons (e.g., R can be a para-phenylene). The alkylene or arylene can be substituted or unsubstituted. $R^1$ can be —OH or —OCH$_2$CH$_2$OCH$_2$CH$_2$OCH$_3$. $R^2$ can be the same or different and can be bivalent alkylene or arylene having from about 1 to about 18 carbons. The alkylene or arylene can be substituted or unsubstituted. $R^2$, by virtue of its own structure, can create a monocyclic structure with the —BOO group or it can form a bicyclic or polycyclic structure. Embodiments of a monocyclic structure include, for example, where $R^2$ is 2,3-dimethyl-2,3-butene or 1,3 propene. An embodiment of $R^2$ creating a bicyclic structure includes where $R^2$ is ortho-phenylene.

Some embodiments of the coupling compound include

The coupling compound can be produced using a variety of methods, including, for example, those discussed and cited in Leino & Lonnqvist, *Tetrahedron Letters*, Vol. 45, pp. 8489-91 (2004). For example, sulfuryl chloride can be mixed with one or more thiols to provide combinations of disulfides. In some instances, where there is a single thiol, a symmetric disulfide will result. Gaseous hydrochloric acid and sulfur dioxide produced from the reaction and, in some instances, are eliminated from the reaction mixture by allowing them to evaporate out of the system or by using a vacuum or a rotary evaporator. The reaction can take place with or without (i.e., neat) solvent. The solvent can be any solvent that allows the reaction to take place, including for example, methylene chloride, chloroform, or acetone. The reaction temperature can be, for example, about room temperature or about 0° C. and can be controlled using, for example, an ice bath. To increase the number of sulfurs in the coupling compound (i.e., n), any known method can be used including, for example, those described by Grant & van Wazer, *J. Am. Chem. Soc.*, Vol. 86, pp. 3012-3017 (1964).

Some embodiments of synthesis of the coupling compound include

Other embodiments including $R^2$ can be similarly synthesized, such as

The coupling compound can be incorporated into a rubber composition. Rubber compositions can be comprised of the coupling compound, coupling agent (e.g., coupling agents other than the coupling compound), polymer, and filler. The rubber compositions can further include vulcanizing agents, process oils, vulcanizing accelerators and other additives.

The amount of coupling compound can be from about 0.05 to about 10.0 phr or from about 0.1 phr to about 5.0 phr. In other embodiments, the amount of coupling agent can be from about 0.5 to about 20 phf or from about 1 to about 10 phf. In still other embodiments, the amount of coupling compound can range from about 1 to about 20 weight percent based on the amount of the silica filler. For example, the amount of coupling compound can be in a range of from about 5 to about 15 weight percent based on the amount of the silica filler.

The polymer can be a single polymer, a mixture of different polymers and can include any type of polymer, including, for example, conventional rubbery polymers. The polymer can be a homopolymer, a copolymer or a terpolymer. The polymer can have a functional group having an affinity for silica. Repeat units and monomers are terms used to describe the makeup of the polymer. A repeat unit differs from a monomer in that a double bond of the monomer is consumed by the polymerization reaction to provide a repeat unit that is incorporated into the polymer. Repeat units of the polymer can include those provided from conjugated diene monomers. Examples of the conjugated diene monomer include 1,3-butadiene, isoprene, 1,3-pentadiene, 2,3-dimethylbutadiene, 2-phenyl-1,3-butadiene, and 1,3-hexadiene. The conjugated diene monomer can be used to provide repeat units for a homopolymer, a copolymer, or a terpolymer. Repeat units for the copolymer or terpolymer can be provided from another conjugated diene monomer, a vinyl aromatic monomer, or a functionalized monomer, for example. Examples of the vinyl aromatic hydrocarbon monomer for use in copolymerization with the conjugated diene monomer include styrene, α-methylstyrene, 1-vinylnaphthalene, 3-vinyltoluene, ethylvinylbenzene, divinylbenzene, 4-cyclohexylstyrene, and 2,4,6-trimethylstyrene. Examples of functionalized monomers include those disclosed in U.S. Pat. No. 6,627,721, which is incorporated herein by reference in its entirety, such as 1-[(4-Ethenylphenyl)methyl]-pyrrolidine and 1-[(4-Ethenylphenyl)ethyl]-pyrrolidine.

When carrying out copolymerization using a conjugated diene monomer and a vinyl aromatic hydrocarbon monomer, the monomers, in one example, are 1,3-butadiene and styrene, respectively.

Examples of the initiator for use in the polymerization reaction include organic alkali metal compounds such as organolithium compounds. In one example, the lithium compounds have from about 2 to about 20 carbon atoms. Specific examples include ethyllithium, n-propyllithium, i-propyllithium, n-butyllithium, sec-butyllithium, t-octyllithium, n-decyllithium, phenyllithium, 2-naphthyllithium, 2-butylphenyllithium, 4-phenyl-butyllithium, cyclohexyllithium, 4-cyclopentyllithium, and a reaction product between diisopropenylbenzene and butyllithium. The amount of initiator used includes from about 0.1 to about 20 mmol based on 100 g of monomers.

The polymerization process can be carried out in a solvent, such as a hydrocarbon solvent, that does not destroy the initiator (e.g., organolithium initiators). A suitable solvent may be selected from an aliphatic hydrocarbon, an aromatic hydrocarbon, or an alicyclic hydrocarbon. In one example, the hydrocarbons have from about 3 to about 8 carbon atoms. Examples of the hydrocarbon include propane, n-butane, i-butane, n-pentane, i-pentane, n-hexane, mixed hexanes, cyclohexane, propene, 1-butene, i-butene, trans-2-butene, cis-2-butene, 1-pentene, 2-pentene, 1-hexene, 2-hexene, benzene, toluene, xylene, and ethylbenzene. These solvents may be used alone or in combination; for example, mixed hexanes, cyclohexane, and pentane can be used.

The monomer concentration in the solvent may be for example from about 5 to about 50% by weight. In another example, the concentration may be for example from about 10 to about 30% by weight. When carrying out copolymerization between a conjugated diene monomer and a vinyl aromatic hydrocarbon monomer, the content of the vinyl aromatic hydrocarbon monomer in the monomer mixture charged into a reactor can be for example from about 3 to about 50% by weight. In another example, the content is from about 5 to about 45% by weight.

A modifier may be used when anionic polymerization of a conjugated diene monomer is carried out. The term "modifier" is used herein to mean a compound that has a function to control the microstructure of a conjugated diene polymer and the compositional distribution of monomer units in a copolymer composed of a conjugated diene monomer and a vinyl aromatic hydrocarbon monomer. For example, the increase of the proportion of 1,2-linkage of butadiene portions of a butadiene polymer or in a butadiene portion of a butadiene-styrene copolymer, or the increase of the proportion of the 3,4-linkage of an isoprene polymer can be controlled. In addition, randomization of butadiene units or the styrene units in a butadiene-styrene copolymer, for example, can be controlled. The modifiers are not particularly limited. Examples of the modifiers include ethers such as dimethoxybenzene, tetrahydrofuran, dimethoxyethane, diethylene glycol dibutyl ether, diethylene glycol dimethyl ether, bis(tetrahydrofurylpropane), and tertiary amines such as trimethylamine, pyridine, N-methylmorpholine, N,N,N',N'-tetramethylethylenediamine, and 1,2-dipiperidinoethane. Further examples include potassium salts such as potassium-t-amylate and potassium-t-butoxide and sodium salts such as sodium-t-amylate. The amount to be used of the modifier is within the range of from about 0.01 to about 10 molar equivalents per one mole of the organolithium compound.

Polymerization (e.g., copolymerized or terpolymerized) of the monomer can be carried out utilizing standard temperatures for diene polymerization. Such temperatures can range from about 30° C. to about 110° C., for example. The polymerization reaction can be carried under a pressure generated by the reaction. It can be desirable to carry out the reaction under a pressure sufficient to keep the monomers substantially in a liquid phase. That is, the pressure for the polymerization reaction can depend on the substances to be polymerized, diluents to be used, and polymerization temperatures; higher pressures can be employed if desired. Such a pressure can be obtained by any appropriate method, for example, by pressurizing the reactor by a gas inert to the polymerization reaction.

It can be desirable to remove water, oxygen, carbon dioxide, and other catalyst poison from one or more of the materials, such as initiator, solvent, monomer, and the like, involved in the polymerization process.

A terminating compound can be added to stop the polymerization reaction. Although the timing and method for adding the terminating compound to the polymerization system chain is not particularly limited, such a terminating compound can be added when the polymerization is completed or near completion. In some embodiments, the polymerization is carried out until high conversions of at least about 85 percent are attained. For instance, the terminating compound can be added after a monomer conversion of greater than about 85 percent has been realized.

The polymer (e.g., copolymer or terpolymer) obtained, in one example, can have, for example, a glass transition point (Tg) of −95 to −10° C. as measured by DSC (Differential Scanning Calorimetry) using a heating rate of 10° C./min The Mooney viscosity ($ML_{1+4}/100°$ C.) of the uncured polymer may, for example, be in a range of from about 10 to about 150. In another example, the Mooney viscosity may be, for example, in a range of from about 15 to about 70.

Examples of the conventional rubbery polymer include natural rubber and diene-based synthetic rubbers. Examples of the diene-based synthetic rubbers include emulsion styrene/butadiene copolymers, solution styrene/butadiene copolymers, 1,4-cis-polybutadiene, 1,2-vinyl-polybutadiene, 1,4-cis-polyisoprene, 3,4-polyisoprene, styrene/isoprene/butadiene copolymers, isoprene/butadiene copolymers, styrene/isoprene copolymers, butyl rubber, ethylene/propylene copolymers, and blends thereof. A rubber component, having a branched structure formed by use of a polyfunctional modifier such as tin tetrachloride, or a multifunctional monomer such as divinyl benzene may also be used.

The rubber composition, which includes from about 25% to about 100% by weight polymer (with from about 50% to about 75% weight percent being one embodiment) also can include fillers. In some instances, these fillers can be rubber reinforcing fillers. The filler can be silica, carbon black, or a combination of a silica and a carbon black. Clay and/or organic fillers such as starch can also be used as fillers.

The silica can be a synthetic amorphous rubber reinforcing silica. Examples include wet-process silica (precipitated silica), dry-process silica (fumed silica), calcium silicate, and aluminum silicate. In one example, the silica is precipitated silica.

Examples of various carbon blacks may be found, for example, the Vanderbilt Rubber Handbook, $13^{th}$ Edition (1990) pages 416 through 418.

The amount of the filler used in the rubber composition can be, for example, within a range of from about 10 to about 130 phr (e.g. in a range of from about 20 to about 110 phr).

When synthetic amorphous silica (e.g. precipitated silica) is used as filler in the rubber composition, a silica coupling agent can optionally be used to further increase the reinforcing property at the time when the silica is incorporated. Such silica coupling agents have a moiety reactive with hydroxyl groups (e.g. silanol groups), on the silica filler and another different moiety interactive with the conjugated diene derived elastomer. Examples include organoalkoxymercapto silanes and bis(3-trialkoxysilylalkyl)polysulfides having an average of about 2 to 4 connecting sulfur atoms in its polysulfidic bridge. Examples of the silica coupling agent comprise, for example, bis(3-triethoxysilylpropyl)tetrasulfide, bis(3-triethoxysilylpropyl)disulfide, bis(2-triethoxysilylethyl)tetrasulfide, bis(3-trimethoxysilylpropyl)tetrasulfide, bis(2-trimeth-oxysilylethyl)tetrasulfide, 3-mercaptopropyltrimethoxysilane, 3-mercaptopropyl-triethoxysilane, 2-mercaptoethyltrimethoxysilane, 2-mercaptoethyltriethoxysilane, 3-nitropropyltrimethoxysilane, 3-nitropropyl-triethoxysilane, 3-chloropropyltrimethoxysilane, 3-chloropropyltriethoxysilane, 2-chloroethyltrimethoxysilane, 2-chloroethyltriethoxysilane, 3-trimethoxysilylpropyl-N,N-dimethylthiocarbamoyl tetrasulfide, 3-triethoxysilylpropyl-N,N-dimethylthiocarbamoyl tetrasulfide, 2-triethoxy-silylethyl-N,N-dimethylthiocarbamoyl tetrasulfide, 3-trimethoxysilylpropylbenzothiazole tetrasulfide, 3-triethoxysilyl-propylbenzothiazole tetrasulfide, 3-triethoxysilylpropyl-methacylate monosulfide, 3-trimethoxysilylpropylmethacylate monosulfide, bis(3-diethoxymethylsilylpropyl)tetrasulfide, 3-mercaptopropyldimethoxymethylsilane, 3-nitropropyldimethoxymethylsilane, 3-chloropropyldimethoxymethylsilane, dimethoxymethylsilylpropyl-N,N-dimethyl-thiocarbamoyl tetrasulfide, and dimethoxymethylsilylpropylbenzothiazole tetrasulfide.

The amount of silica coupling agent can be, for example, in a range of from about 1 to about 20 weight percent based on the amount of the silica. In some embodiments, the amount of silica coupling agent can be, for example, in a range of from about 5 to about 15 weight percent based on the amount of the silica.

Examples of vulcanizing agents include sulfur and sulfur containing compounds. The amount of the vulcanizing agent to be used may be for example from about 0.1 to about 10.0 phr. For example, the amount may be from about 1.0 to about 5.0 phr.

Examples of the process oil include for example paraffin-based oils, naphthene-based oils, and aromatic-based oils. The amount to be used of the process oil may be, for example from about 0 to about 100 phr.

The vulcanization accelerators may include for example thiazole-based ones, such as 2-mercaptobenzothiazole, dibenzothiazyl disulfide, and sulphenamides such as for example N-cyclohexyl-2-benzothiazyl sulphenamide, and guanidine-based ones such as for example diphenylguanidine. The amount to be used of the vulcanization accelerator may be, for example, from about 0.1 to about 5.0 phr or from about 0.2 to about 3.0 phr.

The rubber composition of the present invention may also typically contain additives that are conventionally used in rubber industries, for example, are antioxidants, zinc oxide, stearic acid, waxes and antidegradients.

The rubber composition may be obtained by milling the ingredients using a kneading apparatus such as a roll mill, an internal mixer, and the like. After being shaped, the rubber composition can be vulcanized. The rubber composition can be used in various tire components, such as tire treads, under treads, carcasses, side walls, and beads, and in other industrial applications such as rubber cushions, belts, and hoses, for example. In one example, the rubber composition is suitable as a rubber composition for tire treads.

In order to further illustrate the present invention, the following specific examples are given. It should be understood that the examples are not limitations of the scope of the present invention. As used herein, phf means parts per hundred parts filler by weight, phr means parts per hundred parts rubber by weight and % values are by weight unless otherwise specified.

EXAMPLES

Example synthesis of:

To a 500 mL round bottom flask equipped with a stirbar was added a white suspension of 5.00 g (32.5 mmol) of 4-mercaptophenylboronic acid in 300 mL of methylene chloride. The contents were cooled to 0° C. in an ice bath. 2.41 g (17.9 mmol) of $SO_2Cl_2$ was dissolved in 20 mL of methylene chloride and added to the cooled suspension dropwise over 20 minutes. The suspension became yellow in color following addition of the $SO_2Cl_2$. The contents were stirred at 0° C. for 30 minutes. The reaction flask was warmed to room temperature and stirred for an additional hour. The volatiles were removed via rotary evaporation to yield a pale yellow solid in quantitative isolated yield. The material was analyzed by $^1$H NMR spectroscopy and was determined to be of greater than 90% purity and was not purified further.

$^1$H NMR (DMSO-$d_6$): δ 7.46 (d, J=8 Hz, 4H); 7.74 (d, J=8 Hz, 4H); ca. 8 (br s, 4H).

Example of Mixing and Subsequent Testing:

In this experiment, a polymer/silica masterbatch was prepared and mixed with varying amounts of the following coupling compound to generate rubber compositions The polymer/silica masterbatch used in this study contained 100 phr rubber, 73 phr silica, 8.82 phr oil, and 3 phr wax.

One rubber composition was mixed without the addition of any coupling compound, and served as the control. To three additional rubber compositions, the coupling compound described was added at various levels—2 phf, 5.15 phf and 8 phf. In the first non-productive stage, NP1, addition of the coupling compound was the only additive to the polymer/silica masterbatch.

Figure 1:
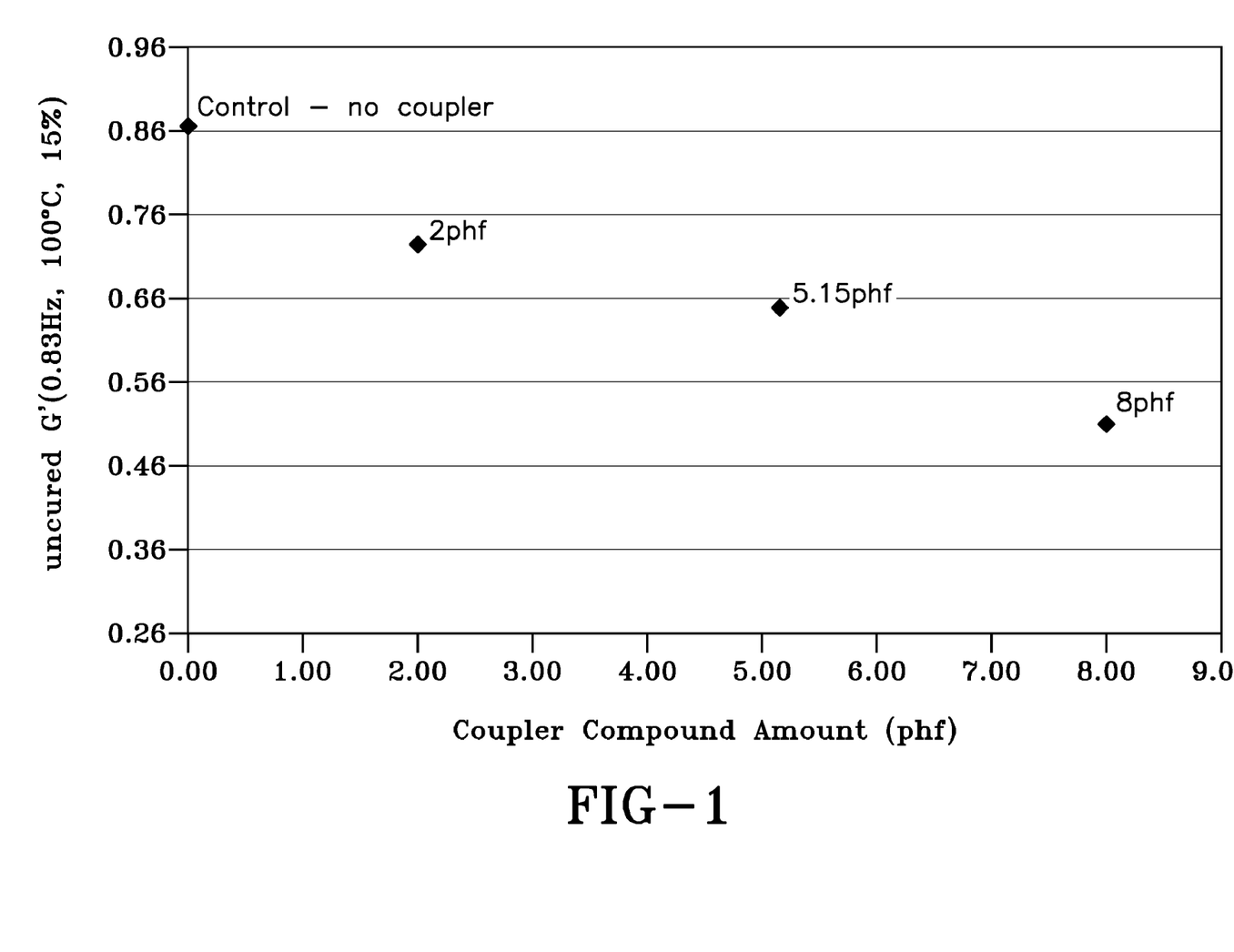
FIG. 1 shows uncured G' as a function of coupling compound amount.

After the first non-productive mixing stage, the resulting rubber compositions were evaluated to determine physical properties. The test data in FIG. 1 was generated from the ASTMD5289 test. FIG. 1 shows uncured G' data, a measure of stiffness, and demonstrates that rubber composition stiffness is lowered with increasing coupling compound loading compared to the control (no coupling compound).

Additional testing was performed after a second non-productive (NP2) mixing stage, at which time identical amounts of other non-curing additives were added to each rubber composition. The resulting rubber compositions were evaluated to determine physical properties.

For all rubber compositions, additives in the NP2 stage were: 10.00 phr carbon black, 0.88 phr ZnO, 2.00 phr diamine antioxidant, 3.50 phr hydrocarbon resin, and 1.50 phr wax.

Filler flocculation and Payne effect were measured using an RPA 2000 instrument. Filler flocculation was measured at 160° C. for 16 minutes. The change in the rubber composition modulus during the thermal treatment was monitored at 1.667 Hz using 0.7% strain. The Payne effect was measured at 40° C. using 1 Hz and 0.28% strain for 16 minutes, and then followed by the strain sweep up to 200% strain.

Initially, the sample was heated to 100° C. to condition the die. Then, the sample was heated to 160° C. and a strain was applied to relax interactions which were the result of the mixing process. The sample remained heated at 160° C., and the increase in G' was measured over time.

When zero coupler or an inefficient coupler is used, the silica agglomerates are larger. Hence, more force is needed to break the agglomerates, which is measured as a higher G', or higher stiffness at the same strain.

Figure 2:
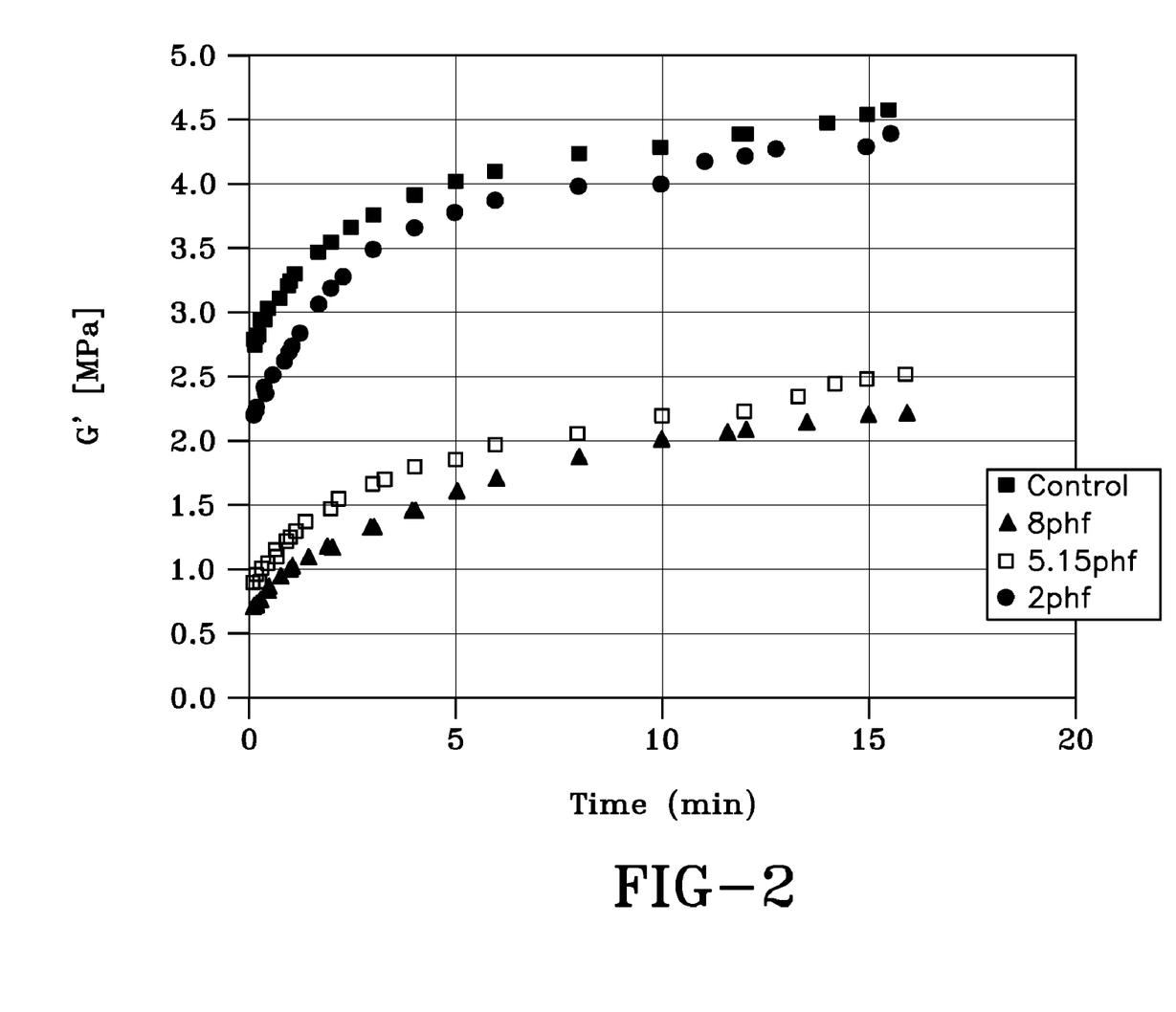
FIG. 2 shows filler flocculation as a function of cure time and coupling compound amount.

As shown in FIG. 2, filler flocculation was reduced for the coupling compound-containing rubber compositions compared to the control. It was also evident that as the level of coupling compound was increased, the filler flocculation was reduced further.

The sample was then cooled to 40° C., and a strain sweep ranging from 0.28%-200% was performed and G' and G" measured. G' can be defined as the "storage modulus" stiffness of the rubber composition. G" can be defined as the "loss modulus" this is the energy lost as heat during the test (as the sample is strained, heat is lost).

Tan delta is G"/G', which is an indicator for hysteresis. A lower value of tan delta is desired, as that indicates that less energy is lost to heat when the rubber composition is stretched and then relaxed. The heat given off during that process indicates a loss of energy.

Figure 3:
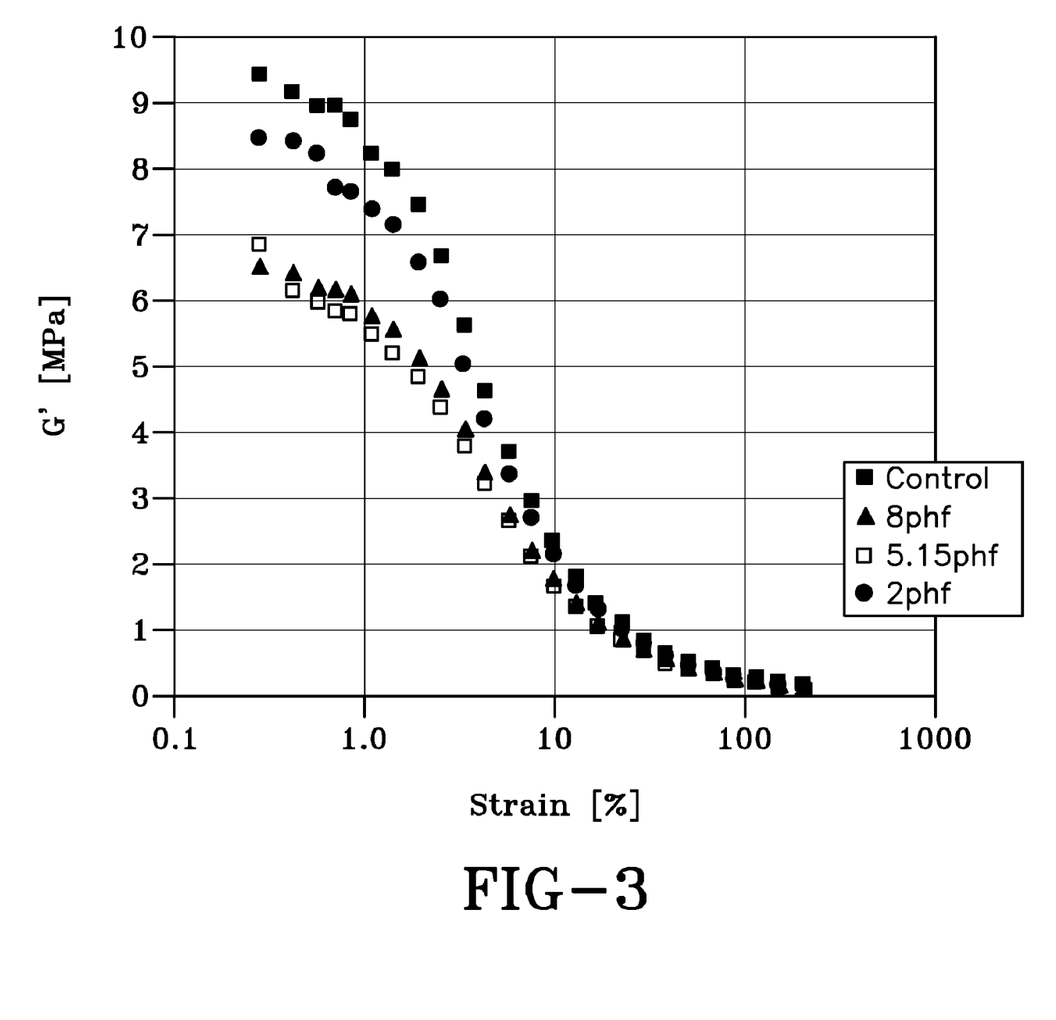
FIG. 3 shows strain dependence of storage modulus for different rubber compositions.

FIG. 3 shows strain dependence of storage modulus for the different rubber compositions. It shows a reduction in the Payne effect for the rubber composition samples in which coupling compound was added. As the coupling compound loading was increased, the Payne effect was reduced further.

Figure 4:
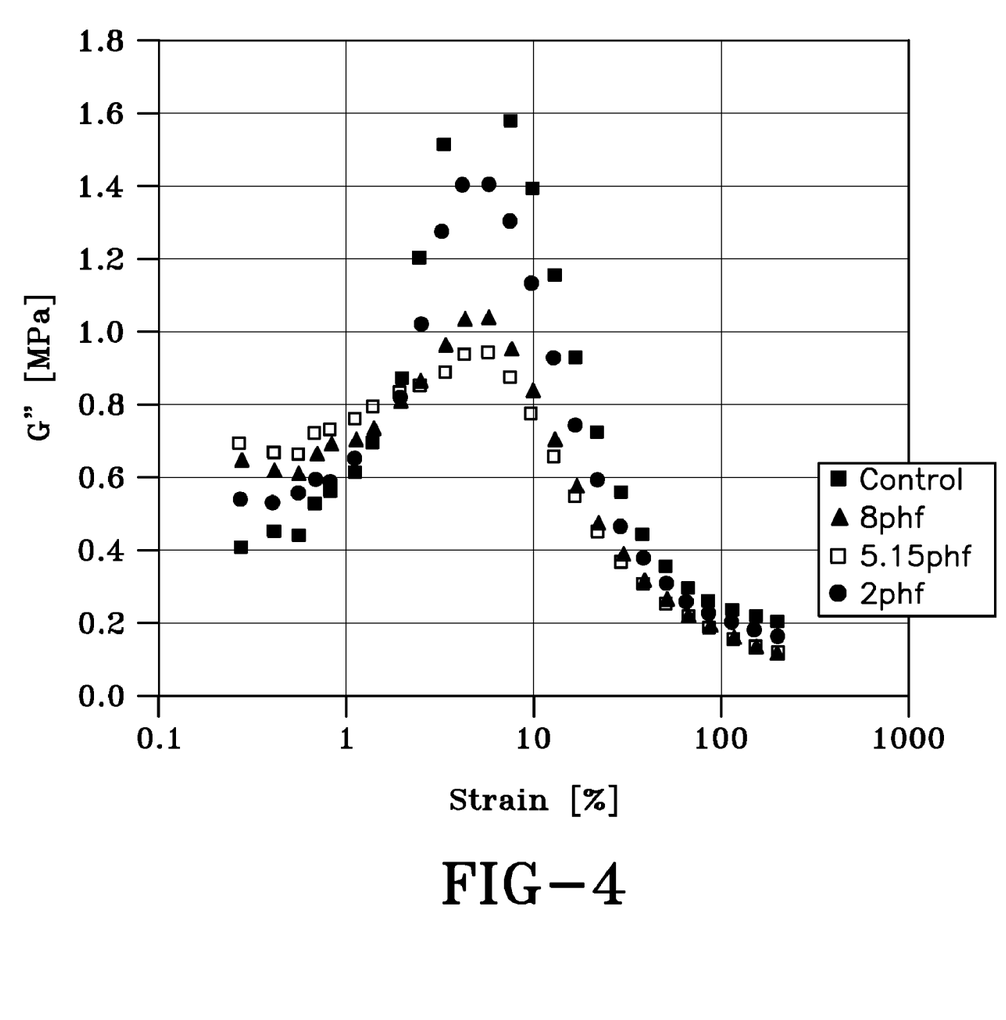
FIG. 4 shows strain dependence of loss modulus for different rubber compositions.

FIG. 4 shows that strain dependence of loss modulus for the different rubber compositions was also reduced for the coupling compound-containing rubber compositions compared to the control. The strain dependence of loss modulus was further reduced with the increase in coupling compound loading.

Figure 5:
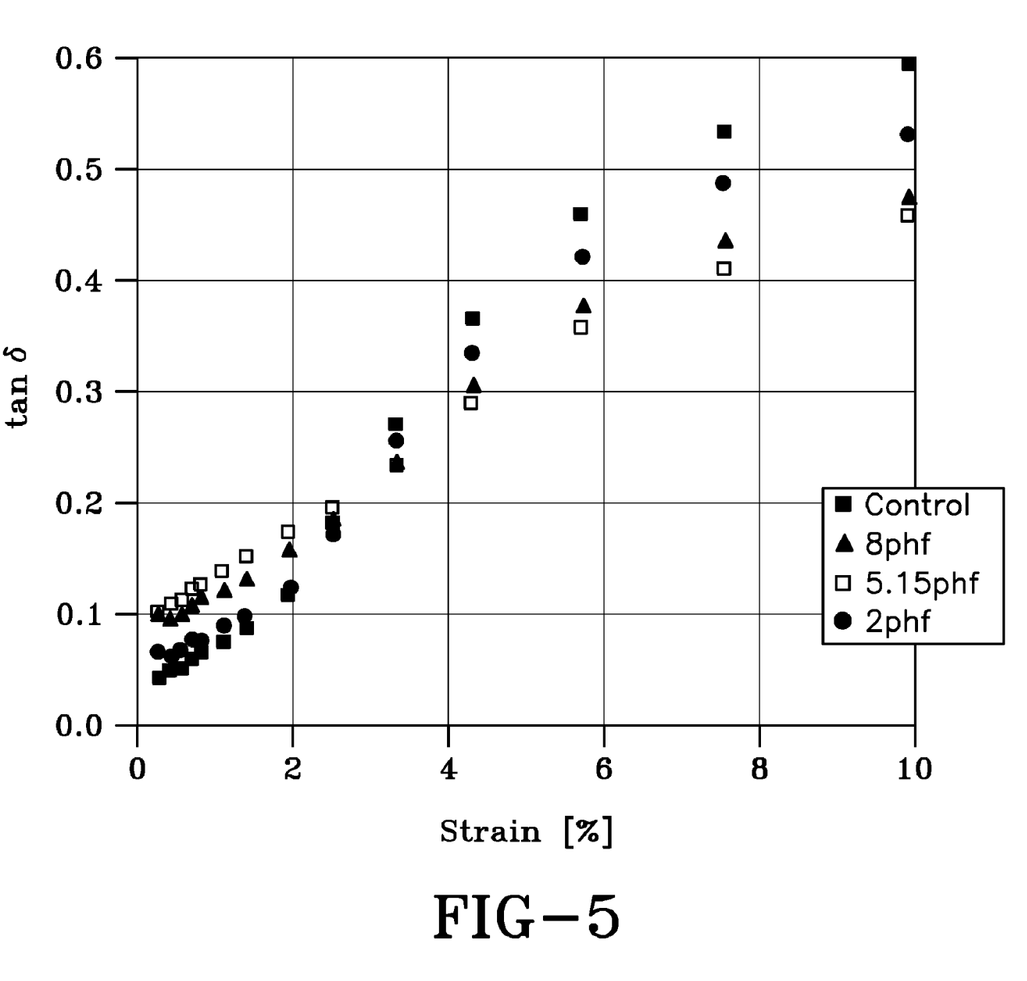
FIG. 5 shows tan delta for different rubber compositions.

FIG. 5 shows that strain dependence of phase angle (tan delta) for the coupling compound-containing rubber compositions was also reduced compared to the control.

While the present invention has been illustrated by the description of one or more embodiments thereof, and while the embodiments have been described in detail, they are not intended to restrict or in any way limit the scope of the appended claims to such detail. Additional advantages and modifications will readily appear to those skilled in the art. The invention in its broader aspects is therefore not limited to the specific details, representative methods and illustrative examples shown and described. Accordingly, departures may be made from such details without departing from the scope of the general inventive concept.

What is claimed is:

1. A coupling compound where n can be the same or different and is 2, 3, or 4; R can be the same or different and is alkylene or arylene with from about 1 to about 18 carbons; $R^1$ can be —OH or —OCH$_2$CH$_2$OCH$_2$CH$_2$OCH$_3$; $R^2$ can be the same or different and is bivalent alkylene or arylene with about 1 to about 18 carbons.

2. The coupling compound of claim 1, wherein $R^2$ is 2,3-dimethyl-2,3-butene, 1,3 propene, or ortho-phenylene.

3. The coupling compound of claim 1, wherein R is para-phenylene.

4. The coupling compound of claim 1, wherein $R^1$ is —OH.

5. The coupling compound of claim 1, wherein the coupling compound is

6. A method for producing a coupling compound comprising (1) mixing SO$_2$Cl$_2$ with (2) recovering respectively, where n can be the same or different and is 2, 3, or 4; R can be the same or different and is alkylene or arylene with from about 1 to about 18 carbons; Rt can be —OH or —OCH$_2$CH$_2$OCH$_2$CH$_2$OCH$_3$; $R^2$ can be the same or different and is bivalent alkylene or arylene with about 1 to about 18 carbons.

7. The method of claim 6, wherein the mixing of SO$_2$Cl$_2$ is with $(R^1)_2$B—R—SH.

8. The method of claim 6, wherein $R^2$ is 2,3-dimethyl-2,3-butene, 1,3 propene, or ortho-phenylene.

9. The method of claim 6, wherein R is para-phenylene.

10. The method of claim 6, wherein $R^1$ is —OH.

11. A rubber composition comprising the coupling compound of claim 1, a polymer, and a filler.

12. The rubber composition of claim 11, wherein the polymer comprises a repeat unit provided from a conjugated diene monomer.

13. The rubber composition of claim 11, wherein the polymer is a homopolymer, a copolymer or a terpolymer.

14. The rubber composition of claim 11, wherein $R^2$ is 2,3-dimethyl-2,3-butene, 1,3 propene, or ortho-phenylene.

15. The rubber composition of claim 11, wherein R is para-phenylene.

16. The rubber composition of claim 11, wherein $R^1$ is —OH.

17. The rubber composition of claim 11, wherein the filler is selected from the group consisting of amorphous silica, rubber reinforcing carbon black, a combination of silica and carbon black, and clay.

18. The rubber composition of claim 11, wherein the filler is selected from the group consisting of precipitated silica, fumed silica, calcium silicate, and aluminum silicate.

19. The rubber composition of claim 11 comprising:
100 parts by weight of a polymer;
10 to 130 phr of a filler; and
a coupling compound from about 1 to about 20 phf.

20. A tire having a component comprising the rubber composition of claim 11.

* * * * *

UNITED STATES PATENT AND TRADEMARK OFFICE
CERTIFICATE OF CORRECTION

PATENT NO. : 7,745,523 B1
APPLICATION NO. : 12/329885
DATED : June 29, 2010
INVENTOR(S) : Robert Alan Woloszynek It is certified that error appears in the above-identified patent and that said Letters Patent is hereby corrected as shown below:

Column 3, Lines 8-10 and Column 9, CLAIM 5, Lines 50-53,

"  " should be

--  --

Column 10
CLAIM 6, Line approximately 25, "Rt can be" should be -- R' can be --

Signed and Sealed this
First Day of February, 2011

David J. Kappos
*Director of the United States Patent and Trademark Office*